United States Patent [19]
Santino et al.

[11] Patent Number: 5,981,841
[45] Date of Patent: Nov. 9, 1999

[54] EARLY SEED 5' REGULATORY SEQUENCE

[75] Inventors: Colleen G. Santino, St. Louis; Timothy W. Conner, Wildwood, both of Mo.

[73] Assignee: Monsanto Company, St. Louis, Mo.

[21] Appl. No.: 08/705,937

[22] Filed: Aug. 30, 1996

[51] Int. Cl.$^6$ .............................. A01H 5/00; C07H 21/04; C12N 5/14; C12N 15/82
[52] U.S. Cl. ........................ 800/298; 435/320.1; 435/419; 536/24.1; 800/287; 800/306; 800/312; 800/314; 800/317.2; 800/317.3; 800/320.1; 800/320.3; 800/322
[58] Field of Search ........................ 536/24.1; 435/320.1, 435/410, 172.3, 419, 69.1, 468; 800/205, 287, 298, 312, 306, 314, 322, 317.3, 317.2, 320.3, 320.1

[56] References Cited

FOREIGN PATENT DOCUMENTS

| 91/13980 A1 | 9/1991 | WIPO | ............................. C12N 15/11 |
| 92/17580 A1 | 10/1992 | WIPO | ............................. C12N 05/10 |
| 93/20216 | 10/1993 | WIPO | ............................. C12N 15/82 |

OTHER PUBLICATIONS

Plant AL, et al. "Regulation of an Arabidopsis oleosin gene promoter in transgenic tobacco." Plant Mol. Biol. 25: 193–205.
Asako, et al., (1995) *Plant Cell Reports*, 14:539–544.
Bearson, et al., (1993) *Plant Molecular Biology*, 22:255–267.
Barker, et al., (1988) *Proceedings of the National Academy of Sciences, USA*, 85:458–462.
Bustos, et al. (1988) *Plant Cell,* 1:839–853.
Callis, et al., (1987) *Genes and Development,* 1:1183–1200.
Conceicao, et al. (1994) *The Plant Journal,* 5(4):493–505).
Datta et al. (1993) *Plant Molecular Biology,* 21:859–869.
Delannay, et al., (1995) *Crop Science,* 35:1461–1467.
Dietrich, et al. (1992) *The Plant Cell,* 4:1371–1382.
Domanskii, et al., (1993) *Biopolimery Kletka,* 9:3–9.
Donath, et al., (1995) *Plant Molecular Biology,* 28:667–676.
Ericson, et al., (1991) *European Journal of Biochemistry,* 197:741–746.
Frohman (1990) *PCR Protocols: A Guide to Methods and Applications,* Academic Press, San Diego, pp. 28–38.
Garbarino, et al., (1995), 109:1371–1378.
Gamborg, et al. (1968) *Experimental Cell Research,* 50:151–158.
Hobbs, et al., (1990) *Plant Cell Reports,* 9:17–20.
Huang, et al., (1997) *Plant Molecular Biology,* 33:125–139.
Kahl, et al., (1995) *World Journal of Microbiology and Biotechnolgy,* 11:449–460.
Kawasaki (1990) *PCR Protocols: A Guide to Methods and Applications,* Academic Press, San Diego, pp. 21–27.

Larkin, et al. (1993) *The Plant Cell,* 5:1739–1748.
Leisey, et al., (1989) *Plant Molecuar Biology,* 14:41–50.
Lelievre, et al., (1992) *Plant Physiology,* 98:387–391.
Lessard, et al., (1993) *Plant Molecular Biology,* 22:873–885.
Maniatis, et al. (1992) *Molecular Cloning: A Laboratory Manual,* Cold Spring Harbor Laboratory Press, Cold Spring Harbor, N.Y.
McClure, et al. (1989) *Science,* 243:91–93.
McKinnon, et al. (1995) *Journal of Cereal Science,* 22:203–210.
Norris, et al., (1993) *Plant Molecular Biology,* 21:895–906.
Schledzewski, et al., (1994) *Transgenic Research,* 3:249–255.
Slightom, et al., (1987) *Planta,* 172:356–363.
Koziel G, et al. "Optimizing expression of transgenes with an emphasis on post–transcriptional events." Plant Mol. Biol. 32: 393–405, 1996.
Benfey PN, et al. "The cauliflower mosaic virus 35S promoter: Combinatorial regulation of transcription in plants." Science 250: 959–966, Nov. 16, 1990.
Kim Y, et al. "A 20 nucleotide upstream element is essential for the nopaline synthase (nos) promoter activity." Plant Mol. Biol. 24: 105–117, 1994.
Hanfler J, et al. Circular extrachromosomal DNA codes for a surface protein in the (+) mating type of the zygomycete Absidia glauca. Curr. Genet. 22: 319–325, 1992.
Datta N, et al. "Isolation and characterization of three families of auxin down–regulated cDNA clones." Plant Mol. Biol. 21: 859–869, 1993.
Datta, N., et al. (Apr. 21, 1993) "Isolation and characterization of three families of auxin down–regulated cDNA clones," *EMBL Sequence Data Library,* Heidelberg, Germany (XP–002051286); Accession No. X69641.
Diaz, I., et al. (1995) "The promoter of the gene Ltr1 from barley confers a different tissue specificity in transgenic tobacco," *Mol. Gen. Genet.* 248:592–598 (XP 002051183).
Nagao, R.T., et al. (1993) "Promoter Analysis of an Auxin–Regulated Gene in Transgenic Plants," *Journal of Cellular Biochemistry* Suppl. O, No. 17 Part A, pp. 120–B385 (XP002052187).

Primary Examiner—Lynette R. F. Smith
Assistant Examiner—Amy J. Nelson
Attorney, Agent, or Firm—Lawrence Lavin, Jr.; Arnold White & Durkee

[57] ABSTRACT

A cotyledon-enhanced 5' regulatory sequence obtainable from soybean that strongly drives gene expression in cotyledons throughout seed development is provided. Also provided are recombinant DNA constructs comprising this 5' regulatory sequence for transformation of plants cells and the production of transgenic plants, as well as an intron and 3' non-coding region useful in modulating gene expression in transformed plant cells.

11 Claims, 8 Drawing Sheets

■ : promoter
▭ : intron
— : 5' untranslated leader
* : translational start site

5,981,841

EARLY SEED 5' REGULATORY SEQUENCE

BACKGROUND OF THE INVENTION

1. Field of the Invention

The present invention relates in general to plant genetic engineering, and in particular to novel 5' and 3' regulatory sequences, including a novel intron contained within the leader of the 5' regulatory sequence, useful in the expression of genes in plants during early seed development and throughout seed development. These regulatory sequences can be operably linked to DNAs encoding selected protein products, and the combinations can be incorporated into recombinant vectors to facilitate the expression of these DNAs in transgenic plants.

2. Description of Related Art

The expression of a plant gene existing in the form of double stranded DNA involves transcription of messenger RNA (mRNA) from one strand of the DNA by RNA polymerase and subsequent processing of the MRNA primary transcript inside the nucleus. This processing involves a 3' non-coding region which adds polyadenylate nucleotides to the 3' end of the MRNA.

Transcription of DNA into mRNA is regulated by a region of DNA usually referred to as the promoter. The promoter region contains a sequence of bases that signals RNA polymerase to associate with the DNA and initiate the transcription of mRNA using one of the DNA strands as a template to make a corresponding complementary strand of RNA.

Recent advances in genetic engineering have provided the requisite tools to transform plants to contain and express foreign genes (Kahl et al. (1995) World Journal of Microbiology and Biotechnology 11: 449–460). It is now possible to produce plants that have unique characteristics of agronomic and crop processing importance. The ability to select the tissues in which to express such foreign genes and the time during plant growth in which to obtain expression of such foreign genes is possible through the choice of appropriate promoters that turn on these genes. A wide range of promoters is known for various plants, plant tissues, and developmental stages (McKinnon et al. (1995) Journal of Cereal Science 22: 203–210; Baerson et al. (1993) Plant Molecular Biology 22: 255–267; Domanskii et al. (1993) Biopolimery Kletka 9:3–18).

The soybean is an important plant for genetic engineering as it can be transformed to express foreign genes (Delannay et al. (1995) Crop Science 35: 1461–1467), and because it possesses valuable characteristics that can be improved by introducing certain genes.

Promoters useful in expressing foreign genes in soybean seeds and other seeds/cotyledons are known. For example, promoters from genes encoding seed storage proteins of various dicotyledonous plants have been identified. The major seed storage protein in soybean is β-conglycinin. The promoters from both the α' and β subunits of β-conglycinin have been identified (Slighton et al. (1987) Planta 172: 356–363; Barker et al. (1988) Proceedings of the National Academy of Sciences, USA 85: 458–462). Promoters from genes encoding seed storage proteins of other species are also known. Two 2S albumin promoters of Arabidopsis thaliana have been identified (Conceicao et al. (1994) The Plant Journal 5(4): 493–505), the promoter of a 2S albumin gene of Brassica napus has been identified (Mats et al. (1991) European Journal of Biochemistry 197: 741–746), and a promoter from the β-phaseolin gene of Phaseolus vulgaris has been identified (Bustos et al. (1988) Plant Cell 1: 839–853). Since seed storage proteins accumulate to high levels in seeds, the promoters from these genes have the potential to drive the expression of target genes to high levels in seeds of transgenic plants.

In addition to the promoter, the 5' untranslated regions of genes, introns from genes, and the 3' non-coding regions of genes have also been observed to play significant roles in the regulation and enhancement of gene expression. For example, 5' untranslated leaders have been observed to increase transient expression of heterologous genes (Hobbs et al. (1990) Plant Cell Reports 9: 17–20). Introns have also been observed to increase transient expression of heterologous genes (Callis et al. (1987) Genes and Development 1: 1183–1200). In addition to enhancing gene expression, introns that function in the regulation of gene expression have also been identified. For example, the GapAl promoter from maize requires the first intron of the GapA1 gene as well as surrounding exon border sequences in order to express in cultured cells (Donath et al. (1995) Plant Molecular Biology 28: 667–676). 3' noncoding regions of genes have also been observed to be involved in the regulation of gene expression. For example, enhancers contained within the 3' noncoding regions of genes have been required for the activation of tissue-specific expression in promoter-GUS fusions (Dietrich et al. (1992) The Plant Cell 4: 1371–1382; Larkin et al. (1993) The Plant Cell 5: 1739–1748).

The use of promoters from seed storage protein genes to drive the expression of heterologous genes in transformed plants is limiting in that storage proteins are predominantly expressed late in seed development, i.e., only during the midmaturation stages of development. Thus, there is a need for strong promoters that facilitate expression of genes during early seed development. Promoters active during early seed development possess the advantage of causing the selective accumulation of desirable gene products in seeds during early seed development, facilitating the enhanced production and accumulation of such desirable gene products in seeds, i.e., plant tissues that can be conveniently and economically harvested and processed.

While present technology permits the transformation of plants with genes encoding selected products, the expression of such genes is either ubiquitous if the promoter is constitutive, or is regulated in a temporal or tissue-dependent manner if the promoter is stage- or tissue-specific. Continuous expression precludes production at particular stages or in specific tissues, and can adversely affect yield due to increased energy demands associated with prolonged synthesis of the product. Tissue- or stage-specific expression permits greater control over the temporal and spatial accumulation of desired products. Thus, promoter sequences that control the expression of desired genes in a tissue-specific, stage-specific manner that can be employed in recombinant constructs for the transformation of plants, and that would facilitate greater control over the location and timing of expression of introduced genes and reduce the possibility of deleterious effects on overall plant growth, are highly desirable.

SUMMARY OF THE INVENTION

Accordingly, the present inventors have sought and discovered a seed-enhanced 5' regulatory region, comprising a promoter, non-translated leader sequence, and intron within the leader, that permits control over the spatial and temporal expression of selected genes in plants, i.e., in cotyledons during early seed development and subsequently throughout further seed development. This 5' regulatory sequence, which is a DNA fragment of about 2.0 kb comprising the nucleotide sequence shown in SEQ ID NO:7, has been derived from the ADR12-2 gene of soybean, which is down-regulated by auxin (Datta et al. (1993) Plant Molecular Biology 21: 859–869). The intron contained within the 5' non-translated leader sequence is a DNA fragment of approximately 0.4 kb, comprising the nucleotide sequence shown in SEQ ID NO:8. Also provided is a 3' non-coding region of about 1.2 kb, comprising the nucleotide sequence shown in SEQ ID NO: 10.

In particular aspects, the present invention includes:

An isolated DNA molecule, comprising a 5' regulatory sequence that directs transcription of a gene throughout seed development in plants. This isolated DNA molecule can have a size of about 2.0 kb, can comprise the 5' regulatory sequence of gene ADR12-2 of soybean, and can comprise the nucleotide sequence shown in SEQ ID NO:7.

A recombinant, double-stranded DNA molecule expressible in plant cells, comprising operatively linked in sequence in the 5' to 3' direction:
  (a) a 5' regulatory sequence that directs transcription of a gene throughout seed development in plants;
  (b) a structural DNA sequence that encodes an RNA sequence which encodes a desired protein, or a structural DNA sequence that encodes an RNA sequence in antisense;
  (c) a 3' non-coding region which encodes a polyadenylation signal which functions in plant cells to cause transcriptional termination and the addition of polyadenylate nucleotides to the 3' end of said RNA sequence which encodes a desired protein or said RNA sequence in antisense; and optionally,
  (d) a 3' non-coding region which contains a sequence involved in modulating activity of said 5' regulatory sequence;
  wherein said 5' regulatory sequence is heterologous with respect to said structural DNA sequence.

The 5' regulatory sequence of the foregoing recombinant, double-stranded DNA molecule can have a size of about 2.0 kb, can comprise the 5' regulatory sequence of gene ADR12-2 of soybean, and can comprise the nucleotide sequence shown in SEQ ID NO:7.

A transformed plant cell, containing a recombinant, double-stranded DNA molecule expressible in plant cells, comprising operatively linked in sequence in the 5' to 3' direction:
  (a) a 5' regulatory sequence that directs the transcription of a gene throughout seed development in plants;
  (b) a structural DNA sequence that encodes an RNA sequence which encodes a desired protein, or a structural DNA sequence that encodes an RNA sequence in antisense;
  (c) a 3' non-coding region which encodes a polyadenylation signal which functions in plant cells to cause transcriptional termination and the addition of polyadenylate nucleotides to the 3' end of said RNA sequence which encodes a desired protein or said RNA sequence in antisense; and optionally,
  (d) a 3' non-coding region which contains a sequence involved in modulating activity of said 5' regulatory sequence;
  wherein said 5' regulatory sequence is heterologous with respect to said structural DNA sequence.

The 5' regulatory sequence present in the recombinant, double-stranded DNA molecule of the foregoing transformed plant cell can have a size of about 2.0 kb, can comprise the 5' regulatory sequence of gene ADR12-2 of soybean, and can comprise the nucleotide sequence shown in SEQ ID NO:7.

A transgenic plant, cells of which contain a recombinant, double-stranded DNA molecule expressible in plant cells, comprising operatively linked in sequence in the 5' to 3' direction:
  (a) a 5' regulatory sequence that directs the transcription of a gene throughout seed development in plants;
  (b) a structural DNA sequence that encodes an RNA sequence which encodes a desired protein, or a structural DNA sequence that encodes an RNA sequence in antisense;
  (c) a 3' non-coding region which encodes a polyadenylation signal which functions in plant cells to cause transcriptional termination and the addition of polyadenylate nucleotides to the 3' end of said RNA sequence which encodes a desired protein or said RNA sequence in antisense; and optionally,
  (d) a 3' non-coding region which contains a sequence involved in modulating activity of said 5' regulatory sequence;
  wherein said 5' regulatory sequence is heterologous with respect to said structural DNA sequence.

The 5' regulatory sequence present in the recombinant, double-stranded DNA molecule of the cells of the foregoing transgenic plant can have a size of about 2.0 kb, can comprise the 5' regulatory sequence of gene ADR12-2 of soybean, and can comprise the nucleotide sequence shown in SEQ ID NO:7.

A method of expressing a gene in a transgenic plant, comprising:
  (a) transforming plant cells with a recombinant DNA molecule comprising operatively linked in sequence in the 5' to 3' direction:
    (i) a 5' regulatory sequence that directs the transcription of a gene throughout seed development in plants;
    (ii) a structural DNA sequence that encodes an RNA sequence which encodes a desired protein, or a structural DNA sequence that encodes an RNA sequence in antisense;
    (iii) a 3' non-coding region which encodes a polyadenylation signal which functions in plant cells to cause transcriptional termination and the addition of polyadenylate nucleotides to the 3' end of said RNA sequence which encodes a desired protein or said RNA sequence in antisense; and optionally,
    (iv) a 3' non-coding region which contains a sequence involved in modulating activity of said 5' regulatory sequence;
    wherein said 5' regulatory sequence is heterologous with respect to said structural DNA sequence;
  (b) selecting plant cells that have been transformed;
  (c) regenerating plant cells that have been transformed to produce differentiated plants; and
  (d) selecting a transformed plant which expresses said structural DNA sequence.

The 5' regulatory sequence present in the recombinant, double-stranded DNA molecule of the foregoing method can have a size of about 2.0 kb, can comprise the 5' regulatory sequence of gene ADR12-2 of soybean, and can comprise the nucleotide sequence shown in SEQ ID NO:7.

An isolated nucleic acid molecule comprising the nucleotide sequence shown in SEQ ID NO:8.

An isolated nucleic acid molecule comprising the nucleotide sequence shown in SEQ ID NO: 10.

Further scope of the applicability of the present invention will become apparent from the detailed description provided below. However, it should be understood that the detailed description and specific examples, while indicating preferred embodiments of the present invention, are given by way of illustration only, since various changes and modifications within the spirit and scope of the present invention will become apparent to those skilled in the art from this detailed description.

BRIEF DESCRIPTION OF THE DRAWINGS

The above and other aspects, features, and advantages of the present invention will be better understood from the following detailed description taken in conjunction with the accompanying drawings, all of which are given by way of illustration only and are not limitative of the present invention, in which.

DNA fragments common to plasmid maps in FIGS. 1–3are: AMP: ampicillin resistance; ori-pUC: replication origin derived from pUC plasmid; LAC: partial sequence of the lac Z gene; NOS3': 3' polyadenylation sequences of the nopaline synthase (NOS) gene of Agrobacterium Ti plasmid; ori-M13: M13 phage replication origin; GUS:1: coding sequence of β-glucuronidase.

Figure 1:
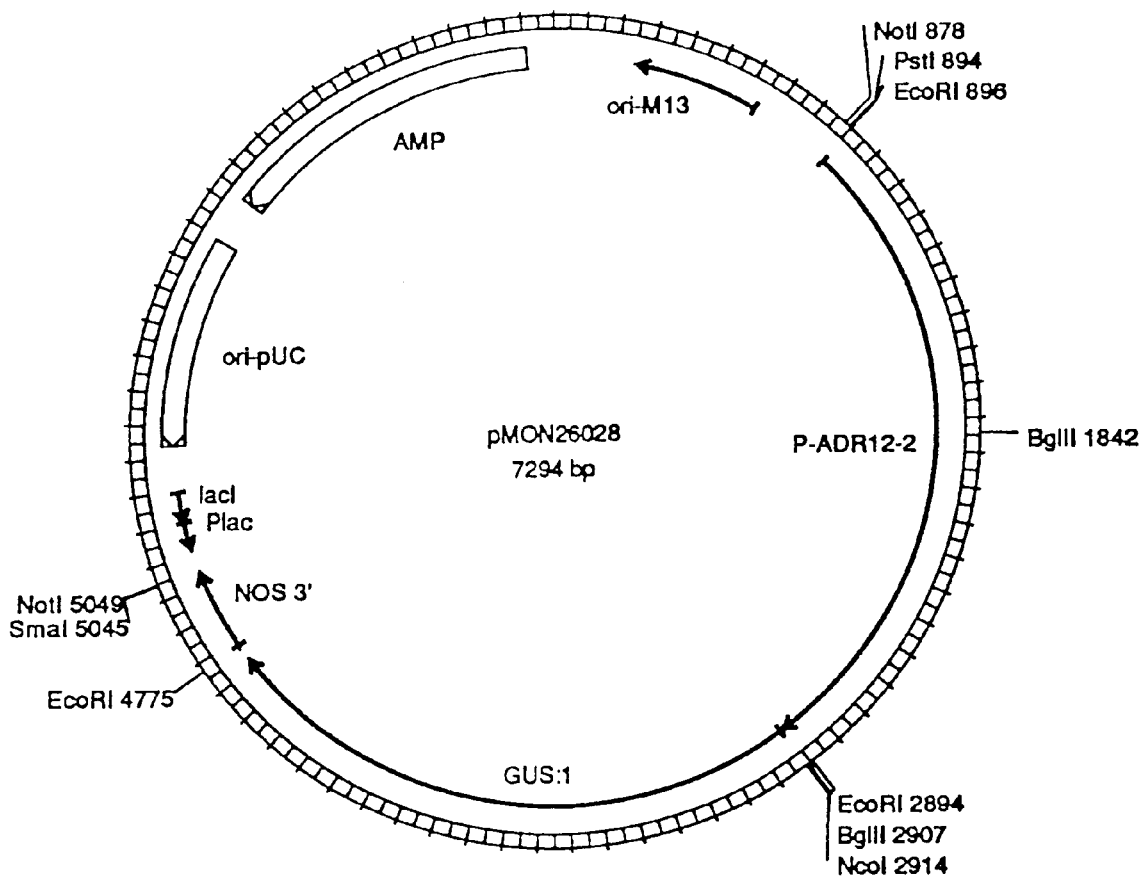
FIG. 1 is a physical map of pMON26028.
Figure 2:
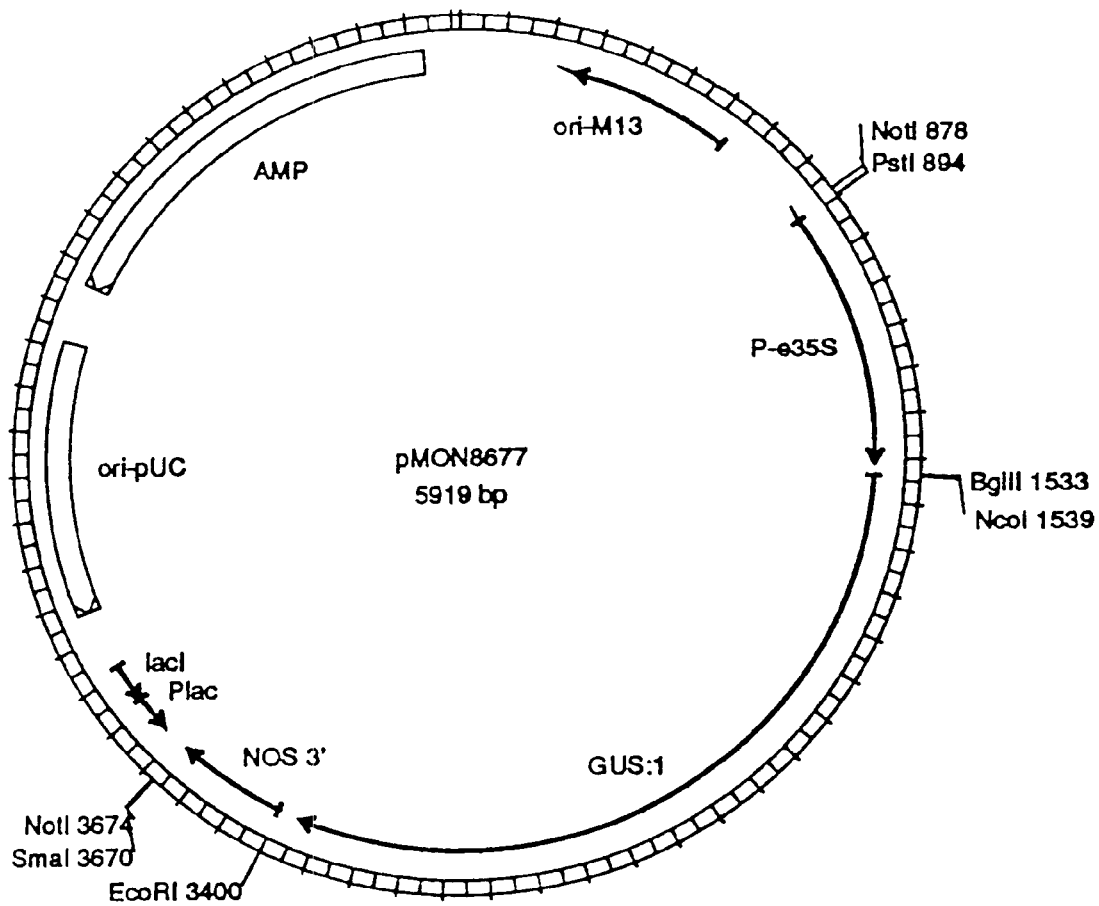
FIG. 2 is a physical map of pMON8677.
Figure 3:
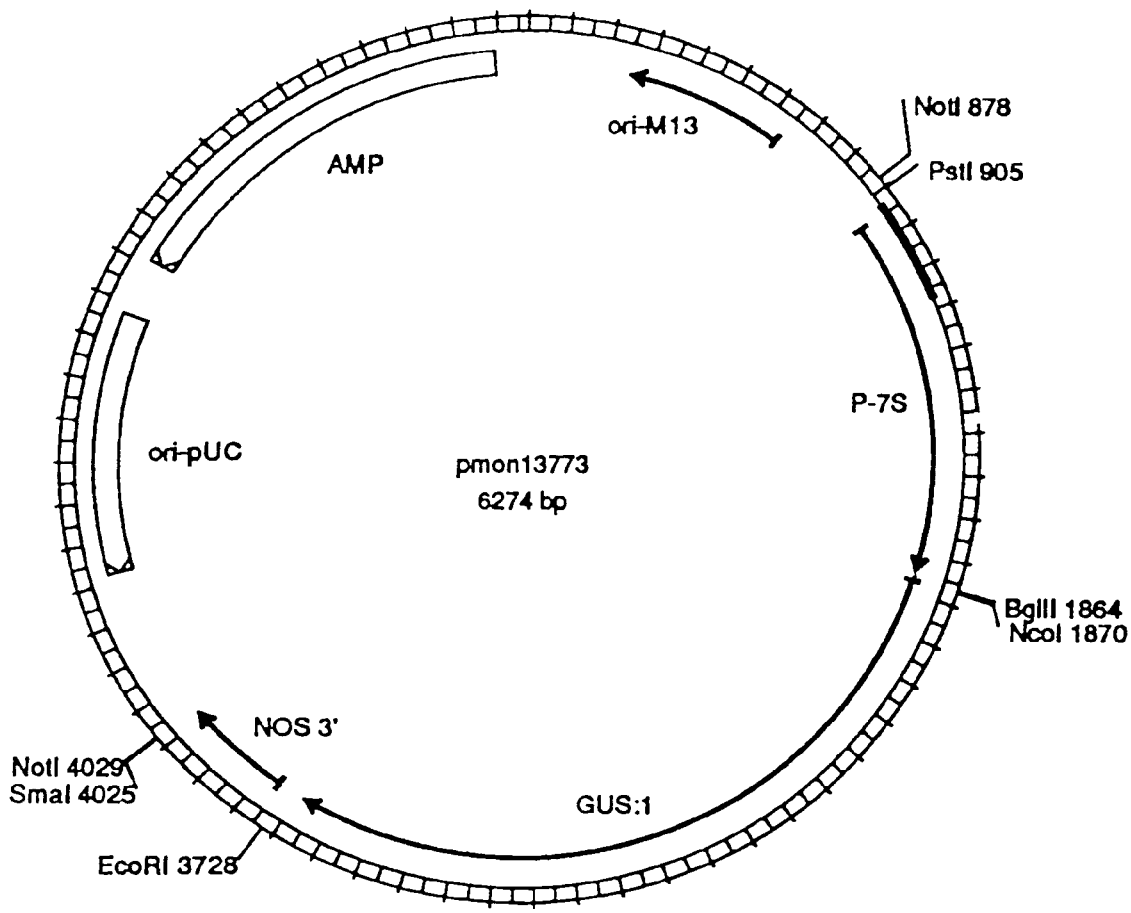
FIG. 3 is a physical map of pMON13773.
Figure 4:
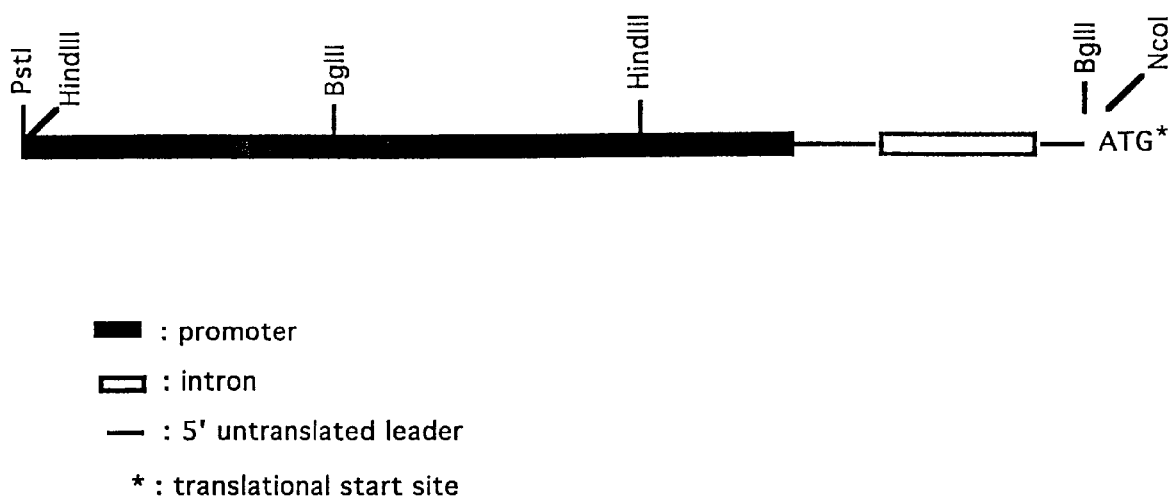

FIG. 4 is a schematic diagram of the ADR12-2 5' regulatory sequence showing various restriction endonuclease digestion sites and regions therein.

Figure 5:
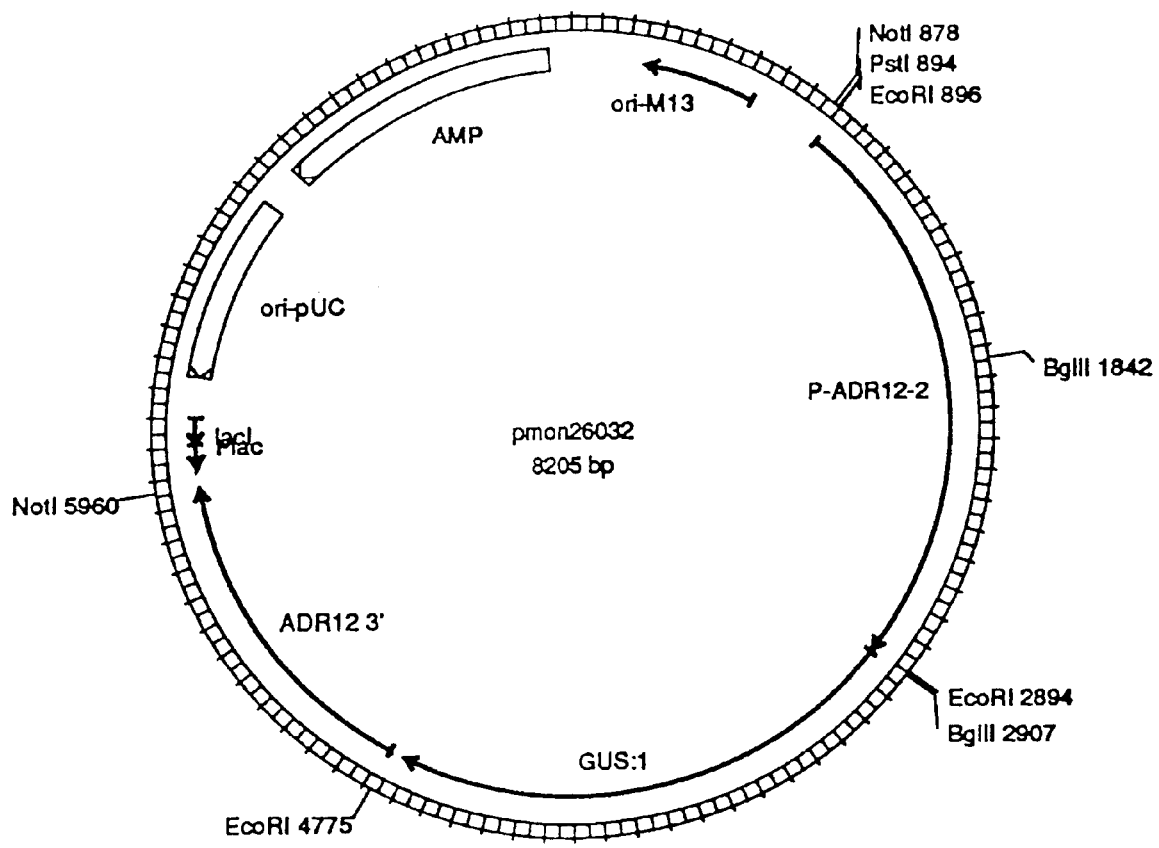

FIG. 5 is a physical map of pMON26032.

DNA fragments contained in pMON26032 common to the other plasmid maps presented above are: AMP: ampicillin resistance; ori-pUC: replication origin derived from pUC plasmid; LAC: partial sequence of the lac Z gene; ori-M13 M13 phage replication origin; GUS: 1: coding sequence of β-glucuronidase.

Figure 6:
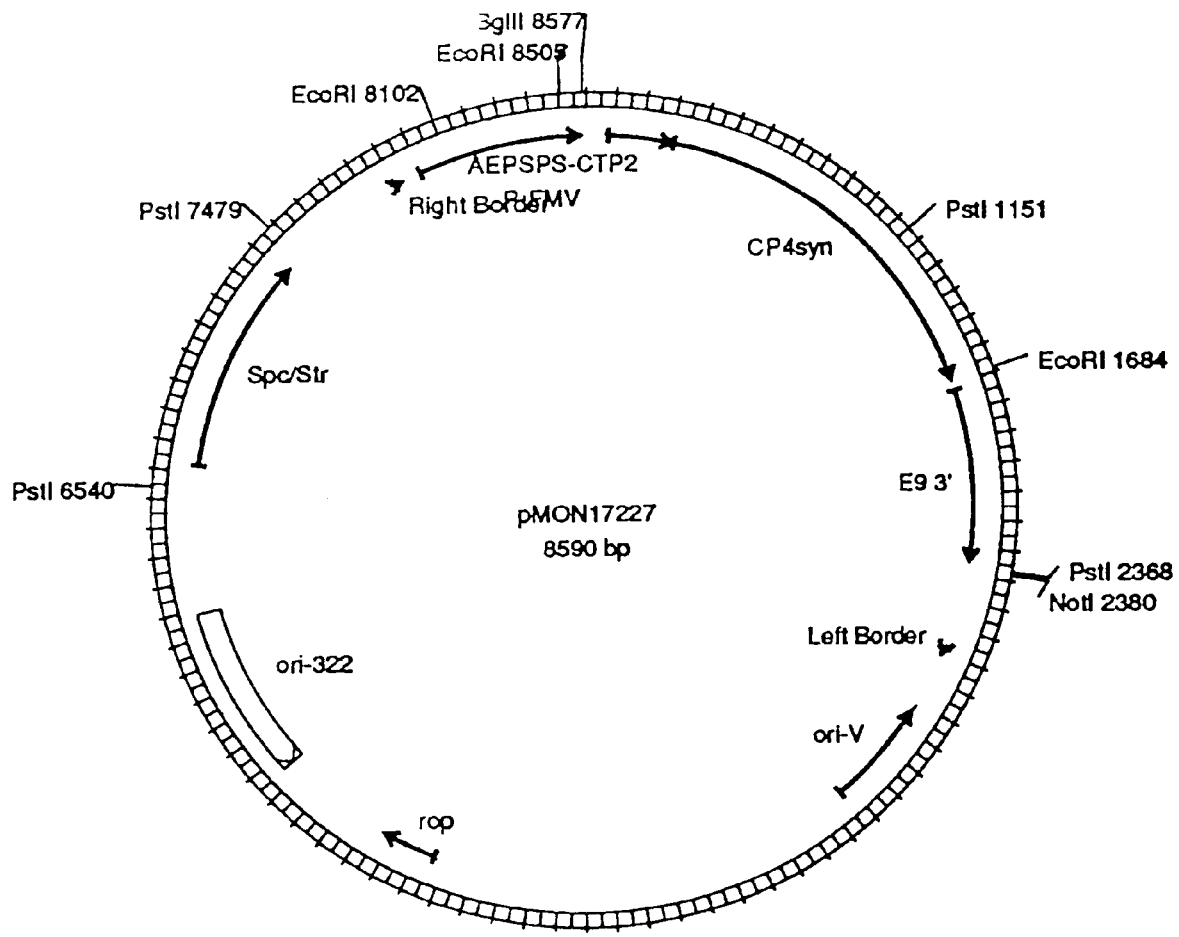

FIG. 6 is a physical map of pMON17227.

Figure 7:
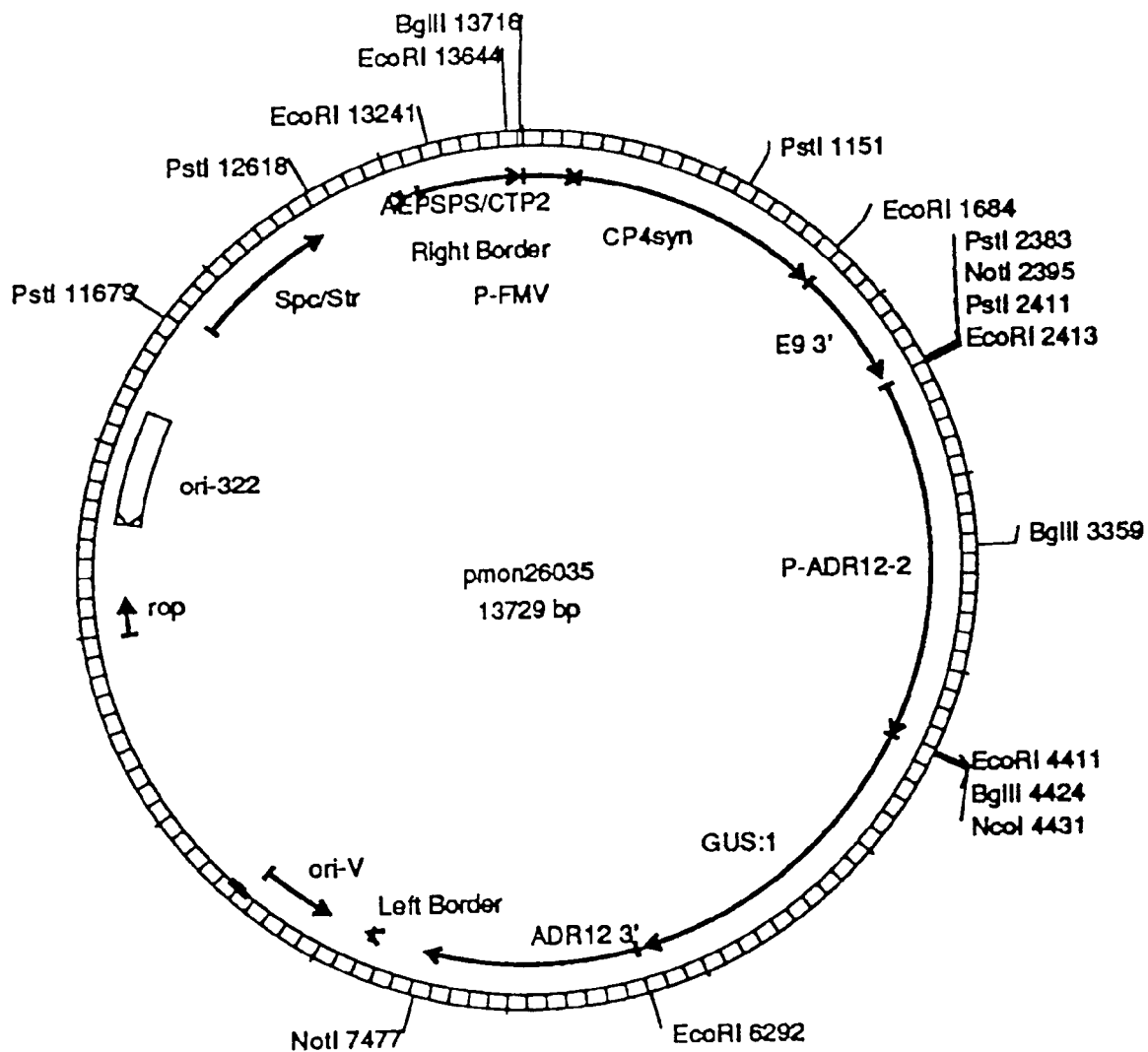

FIG. 7 is a physical map of pMON26035.

Figure 8:
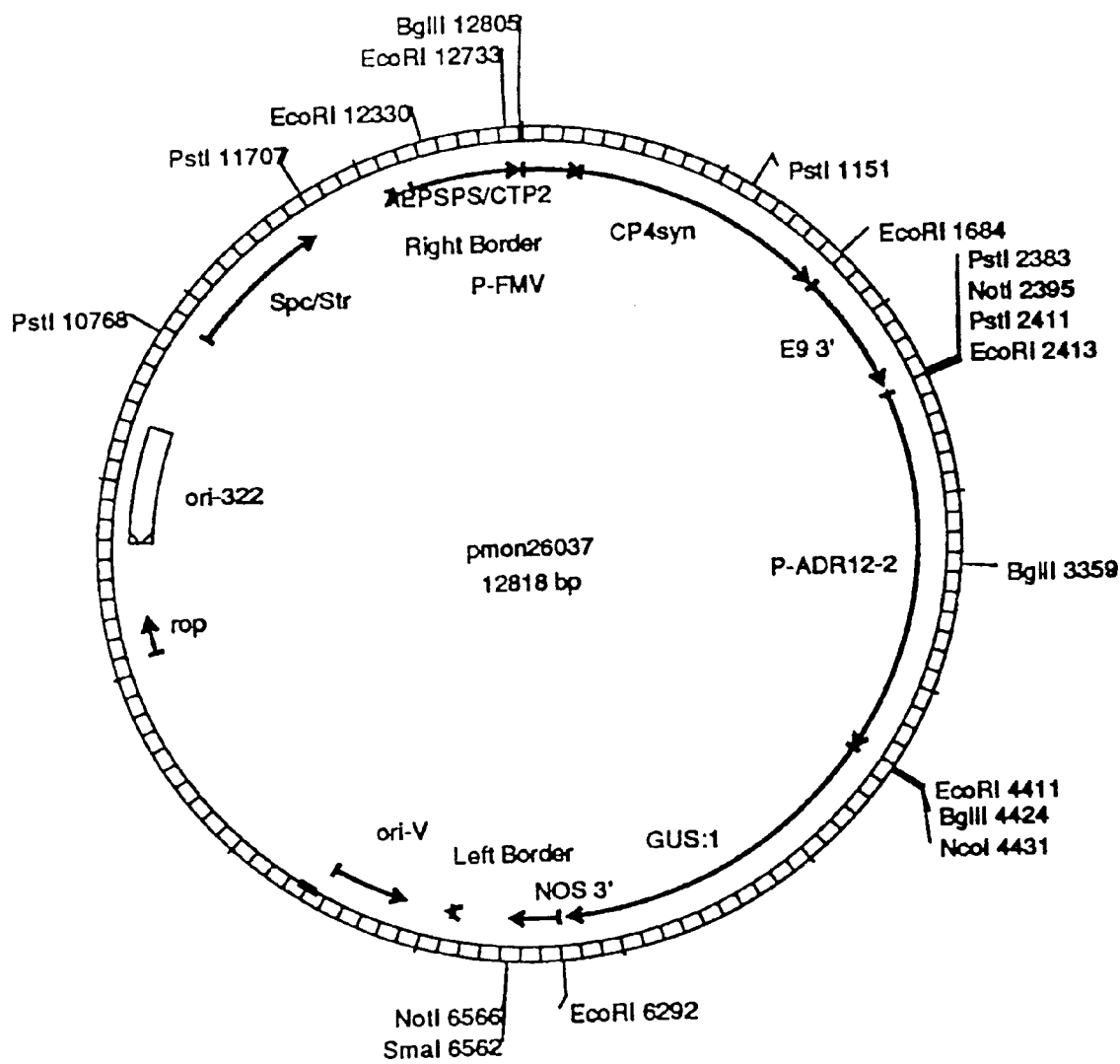

FIG. 8 is a physical map of pMON26037.

DNA fragments common to the plasmid maps in FIGS. 6–8 are: ori-322: origin for *E. coli* replication; Spc/Str: coding sequence of Tn7 adenylyltransferase which confers resistance to spectinomycin and streptomycin; right border: sequences essential for transfer of T-DNA; PFMV: 35S promoter from figwort mosaic virus; AEPSPS-CTP2: first exon of Arabidopsis preEPSP synthase; CP4syn: coding sequence for CP4 EPSP synthase (class II); E9 3': 3' polyadenylation sequences of pea rbcs E9 gene; left border: sequences essential for transfer of T-DNA; ori-V: vegetative origin of replication; rop: coding sequence for repressor of primer.

DESCRIPTION OF ILLUSTRATIVE EMBODIMENTS

The following detailed description is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

The contents of each of the references cited in the present specification are herein incorporated by reference in their entirety.

The seed-enhanced 5' regulatory region of the present invention drives high level expression during the early development of the soybean seed, thereby permitting expression of DNA sequences for selected gene products in developing cotyledons.

A differential screening approach utilizing a soybean seed cDNA library was used to identify cDNA clones that express in seed but not in leaf. cDNA probes, prepared from mRNA extracted from seed at early developmental stages, were employed in this screen. Clones that express abundantly in small seed (1.5–3.0 mm), and that show no detectable expression in leaves, were identified. Genomic Southern analysis indicated that the coding sequence expressed by the 5' regulatory sequence disclosed herein is present in a small (1–2) gene copy number. Detailed RNA blot analysis indicated strong expression in cotyledons (Example 2). Tissue print analysis confirmed the results of the RNA blot analysis, and aided in determining the spatial distribution of the ADR12-2 transcript (Example 3). The 5' regulatory sequence for the gene corresponding to the cDNA clone was then isolated by screening a soybean genomic library (Example 4). The expression pattern of this sequence was confirmed by fusing it to the β-glucuronidase (GUS) gene, and by following the expression of the GUS enzyme with a transient assay system in various tissues and during various developmental stages of cotyledons (Example 5).

Definitions

The following definitions are provided as an aid to understanding the detailed description of the present invention.

The term "expression" refers to the transcription of a gene to produce the corresponding mRNA and translation of this mRNA to produce the corresponding gene product, i.e., a peptide, polypeptide, or protein.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression.

"Homology" refers to the level of similarity between nucleic acid or amino acid sequences in terms of percent nucleotide or amino acid positional identity, respectively, i.e., sequence similarity or identity. Note Reeck et al. (1987) Cell 50: 667 in this regard. Homology also refers to the concept of similar functional properties among different nucleic acids or proteins.

"Hybridization" refers to the ability of a strand of nucleic acid to join with a complementary strand via base pairing. Hybridization occurs when complementary sequences in the two nucleic acid strands bind to one another.

The term "promoter" or "promoter region" refers to a DNA sequence, usually found upstream (5') to a coding sequence, that controls expression of the coding sequence by controlling production of messenger RNA (mRNA) by providing the recognition site for RNA polymerase and/or other factors necessary for start of transcription at the correct site. As contemplated herein, a promoter or promoter region includes variations of promoters derived by means of ligation to various regulatory sequences, random or controlled mutagenesis, and addition or duplication of enhancer sequences. The promoter region disclosed herein, and biologically functional equivalents thereof, are responsible for driving the transcription of coding sequences under their control when introduced into a host as part of a suitable recombinant vector, as demonstrated by its ability to produce mRNA.

The term "recombinant DNA construct" or "recombinant vector" refers to any agent such as a plasmid, cosmid, virus, autonomously replicating sequence, phage, or linear or circular single-stranded or double-stranded DNA or RNA nucleotide sequence, derived from any source, capable of genomric integration or autonomous replication, comprising a DNA molecule in which one or more DNA sequences have been linked in a functionally operative manner. Such recombinant DNA constructs or vectors are capable of introducing a 5' regulatory sequence or promoter region and a DNA sequence for a selected gene product into a cell in such a manner that the DNA sequence is transcribed into a functional mRNA which is translated and therefore expressed.

"Regulatory sequence" refers to a nucleotide sequence located upstream (5'), within, and/or downstream (3') to a DNA sequence encoding a selected gene product whose transcription and expression is controlled by the regulatory sequence in conjunction with the protein synthetic apparatus of the cell.

"Transformation" refers to the introduction of DNA into a recipient host or hosts. "Host" or "hosts" refers to entire plants, plantlets, or plant parts such as plant cells, protoplasts, calli, roots, tubers, propagules, seeds, seedlings, pollen, and plant tissues.

EXAMPLE 1

Differential Screening of a Soybean Seed cDNA Library and Identification of the Seed-Enhanced ADR12-2 cDNA Sequence ADR12-2 was initially identified as a seed-enhanced transcript in a differential screen of a cDNA library.

mRNA Isolation

Total RNA was isolated from soybean (H4994) 1.5–3.0 mm seed as follows. The tissue was ground to a fine powder in liquid nitrogen with a mortar and pestle. Three mls of extraction buffer (50 mM Tris, pH 8, 300 mM NaCl, 5 mM EDTA, pH 8, 0.5 mM aurintricarboxylic acid, 14 mM β-mercaptoethanol, and 2% SDS) were added per gram of tissue. The sample was incubated at 37° C. for 5 minutes, and then centrifuged at 12,000×g for 10 minutes at 4° C. The supernatant was transferred to a tube containing 140 µl of 3M KCl per ml of supernatant transferred. The sample was incubated on ice for 15 minutes and then centrifuged at 3,000×g for 5 minutes at 4° C. The supernatant was then transferred to a tube containing 560 µl of 8M LiCl per ml of supernatant transferred. The sample was incubated overnight on ice, and then centrifuged at 12,000×g for 25 minutes at 4° C. The supernatant was discarded and the precipitate was air dried. The pellet was resuspended in ~1 ml DEPC-treated deionized water per gram of initial starting tissue, depending on pellet size. RNA in the sample was then quantitated spectrophotometrically.

PolyA RNA was isolated from the total RNA using an oligotex-dT mRNA maxikit column (Qiagen) according to the manufacturer's instructions.

cDNA Synthesis

Reverse transcription was performed on 9 µg of polyA RNA by adding 1X buffer (GIBCO BRL), 1 mM dNTPs, 20U RNasin, 50 pmoles oligonucleotide primer (SEQ ID NO:1), and 5U M-MLV reverse transcriptase in a total volume of 20 µl. The reaction mixture was incubated at 42° C. for 1 hour, after which it was loaded on a Quick Spin™ column, Linkers 6 (Boehringer Mannheim Biochemicals) according to the manufacturer's instructions to remove oligonucleotide primers. The DNA sample was then precipitated with 1 µg of glycogen, 1/10 volume 3M sodium acetate (pH 5.3), and 2.5 volumes ethanol at −20° C. overnight. The sample was centrifuged in a microcentrifuge at 10,000 rpm for 10 minutes, the supernatant was discarded, and the pellet was air dried.

The pellet was then resuspended in 18 µl deionized water and tailed with dG by adding 1× TdT buffer (Stratagene), 1 µl of 2 mM dGTP, and 1 µl terminal deoxytransferase. The sample was incubated for 7 minutes at 37° C. and then 5 minutes at 68° C., after which 475 µl deionized water were added.

PCR Amplification

The cDNA ("sample") was amplified via PCR by adding 50 µl of sample to 1× buffer containing $MgCl_2$ (Perkin Elmer), 0.1 mM dNTPs, 2.5U Taq polymerase, and 35 p moles of oligonucleotide primers (0.1 SEQ ID NO:2 : 1 SEQ ID NO:3) in a total volume of 100 µl. One cycle was run (94° C. for 1 minute, 24° C. for 5 minutes, and 72° C. for 10 minutes), followed by 50 cycles (94° C. for 1 minute, 40° C. for 2 minutes, and 72° C. for 2 minutes). The sample was extracted with an equal volume of phenol:chloroform and precipitated, centrifuged, and dried as before. The pellet was then resuspended in 80 µl of deionized water.

The cDNA library was then prepared by digesting the sample to completion with EcoRI, and then extracting, precipitating, centrifuging, and drying as above. The sample was then resuspended in 12 µl of deionized water and quantitated by spotting samples on an agarose plate containing ethidium bromide along with controls. The cDNA library was completed by ligating 90 ng of CDNA insert (sample) with 1 µl of Zap RI CAP vector (Stratagene), and packaging according to the manufacturer's instructions.

The cDNA library was plated and screened according to the manufacturer's instructions. Duplicate plaque lifts were each probed with $^{32}$P-labeled cDNA from either leaf or 1.5–3.0 mm seed. Plasmid rescues were performed on plaques identified as seed positive and leaf negative according to manufacturer specifications, and these plasmids were partially sequenced to further characterize them. Many of the plasmids contained cDNA inserts homologous to the previously reported auxin down- regulated gene ADR12-2 (Datta et al. (1993) Plant Molecular Biology 21: 859–869).

EXAMPLE 2

RNA Blot Analysis of ADR12-2 and β-Conglycinin in Soybean Tissues

Detailed RNA blot analysis was performed to evaluate further the mRNA expression profile of ADR12-2 in soybean tissues.

RNA Isolation and Separation

Total RNA was first isolated from soybean (H4994) seedlings, leaves, stem, root, pod, 1.5–3.0 mm seed, 3.0–5.0 mm seed, 5.0–7.0 mm cotyledons, 7.0–9.0 mm cotyledons, 9.0–11.0 mm cotyledons, embryo axis from 7.0–11.0 mm seed, and seed coat from 7.0–11.0 mm seed using the same method employed in Example 1.

RNA-denaturing formaldehyde gels were run loading 10 µg of each RNA sample per lane (Maniatis et al. (1982) Molecular Cloning: A Laboratory Manual, Cold Spring Harbor Laboratory Press, Cold Spring Harbor, N.Y.). The RNA was transferred onto nitrocellulose via capillary action. The nitrocellulose containing RNA was washed in 2× SSC, air dried, and baked at 80° C. for 30 minutes. Each blot was then prehybridized in 10 mls of prehybridization solution (20× SSC, 50× Denhardt's solution, 20% SDS, 0.5M NaPO$_4$, pH 6.5, and 20 μl of yeast RNA (20 mg/ml)) at 61° C. for ~3 hours, after which the probe was added. Blots were probed with $^{32}$P-labeled sequences from both β-conglycinin and ADR12-2.

Probe Preparation and Hybridization

The probe sequences for ADR12-2 were obtained from the rescued plasmids of the ADR12-2 cDNA clone identified in the initial cDNA library screen described in Example 1. The probe sequences for β-conglycinin were obtained via reverse transcription of mRNA followed by PCR amplification as follows. The region of β-conglycinin amplified was identical to a 394 base pair fragment of the α' subunit, which is 92% similar to the α subunit, and 87% similar to a 71 base pair region of the β subunit. This probe can therefore be used to detect all three subunits of β-conglycinin. SEQ ID NO:4 shows the sequence of the oligonucleotide primer used in the forward polymerization reaction. It contains a SalI restriction enzyme site for cloning purposes, followed by 20 nucleotides homologous to the α' subunit of β-conglycinin. SEQ ID NO:5 shows the sequence of the oligonucleotide primer used in the reverse polymerization reaction. It contains an EcoRI restriction enzyme site for cloning purposes, followed by 20 nucleotides homologous to the α' subunit of β-conglycinin.

Reverse transcription was first carried out on 2 μg of RNA isolated from 9.0–11.0 mm seed as described above by adding 1× PCR buffer containing MgCl$_2$ (Perkin Elmer), 0.4 mM dNTPs, 20U RNasin, 50 pmoles of each primer, and 40U of M-MLV reverse transcriptase (GFBCO BRL) in a total volume of 25 μl. The reaction mixture was incubated at 25° C. for 10 minutes, and then 42° C. for 1 hour, after which the sample was boiled for 5 minutes and placed on ice. The sample volume was increased to 100 μl maintaining a 1 × buffer concentration, and 2.5U of Taq polymerase were added. The sample was amplified for 30 cycles (94° C. for 1 minute, 40° C. for 2 minutes, and 72° C. for 2 minutes). The PCR product was digested to completion with SalI and EcoRI, and cloned into the same sites in the Stratagene plasmid pBSKS+. Partial sequence analysis was performed to confirm the sequence of the cloned PCR fragment (United States Biolabs Sequenase™ Version 2.0) according to the manufacturer's instructions.

Probes were prepared for detecting both β-conglycinin and ADR12-2 mRNA by digesting each plasmid containing these cDNA sequences to completion with the appropriate restriction enzymes and isolating the DNA fragments containing these cDNA inserts on a 1% low melting temperature agarose gel. Agarose fragments containing the appropriate fragments were removed from the gel. Probes were prepared using Promega Prime-It™ according to manufacturer specifications. Probes were then added to the prehybridizations (20 million cpms) and hybridized overnight at 61° C. The blots were then washed in 2× SSC and 0.1% SDS once for 15 minutes at 25° C., then twice for 15 minutes at 60° C., and finally in 0.2× SSC and 0.1% SDS once for 15 minutes at 60° C. Blots were put on film with an intensifying screen at −80° C. for various exposures, and the bands were evaluated semiquantitatively by visual inspection.

Results

As shown in Table 1, ADR12-2 transcript accumulates in seed throughout development (1.5–11.0 mm), whereas β-conglycinin transcript accumulates later in seed development (5.0–11.0 mm). In addition, ADR12-2 transcript is seed-enhanced, also being present in pod, stem, and seedling. ADR12-2 was expressed weakly, if at all in root, while no ADR12-2 mRNA was observed in leaf

TABLE 1

RNA Blot Analysis of ADR12-2 and β-Conglycinin in Soybean Tissues

|  | ADR 12-2 | B-Conglycinin |
| --- | --- | --- |
| 1.5–3.0 mm seed | ++ | − |
| 3.0–5.0 mm seed | ++ | − |
| 5.0–7.0 mm seed | ++ | + |
| 7.0–9.0 mm cotyledon | ++ | +++ |
| 9.0–11.0 mm cotyledon | +++ | +++ |
| embryo axis | +++ | ++ |
| seed coat | − | +/− |
| pod | ++ | − |
| leaf | − | − |
| root | +/− | − |
| stem | ++ | − |
| seedling with cotyledon | ++ | − |

−: signal not detected
+/−: faint signal detected
+: weak signal, clearly detected
++: moderate signal detected
+++: strong signal detected

EXAMPLE 3

Evaluation of the Spatial Distribution of ADR12-2 Message in Soybean Seed by Tissue Print Analysis Tissue print analysis was performed to evaluate further the spatial distribution of ADR12-2 message in soybean seed and to confirm the RNA blot analysis. Various cross sections of small soybean seed (3.0–6.0 mm) and large soybean seed (9.0–11.0 mm) were tissue printed as described by McClure et al. ((1989) Science 243: 91–93). The tissue prints were probed with radiolabeled, in vitro-synthesized RNAs of ADR12-2 and β-conglycinin sense (negative control) and antisense strands.

cDNA from the plasmids containing ADR12-2 and β-conglycinin sequences (see Example 1) were linearized for in vitro transcription as follows. The plasmid containing ADR12-2 cDNA was digested to completion with either XbaI (for production of antisense transcripts with T3 RNA polymerase) or SalI (for production of sense transcripts with T7 RNA polymerase). The plasmid containing β-conglycinin cDNA was digested to completion with either SalI (for production of antisense transcripts with T7 RNA polymerase) or EcoRI (for production of sense transcripts with T3 RNA polymerase). Each sample was extracted with an equal volume of phenol and chloroform, and precipitated with 1/10 volume of 3M sodium acetate, pH 5.3, and 2.5 volumes of ethanol at −20° C overnight. The samples were then centrifuged at 10,000 rpm in a microcentrifuge for 10 minutes. The supernatants were removed and the pellets were air dried. Each pellet was then resuspended in deionized water.

Radiolabeled probes were prepared via in vitro transcription with $^{32}$P-rCTP as follows. To 1 μg of linearized DNA, 5 μl of 5× transcription buffer (Stratagene), 1 μl each of 10 mM rGTP, rATP, and UTP, 5 μl of 10 mCi/ml α-$^{32}$P-rCTP, and 10U of either T3 or T7 RNA polymerase were added in a total volume of 25 μl. Each reaction mixture was incubated for 30 minutes at 37° C. The RNA transcripts were purified by centrifugation of each sample on a G-50 spin column.

After probing and washing, the prints were put on film at −80° C. A one week exposure of the tissue prints was evaluated visually.

As shown in Table 2, both β-conglycinin and ADR12-2 messages were consistently detected throughout the entire large cotyledons (9.0–11.0 mm), whereas, only ADR12-2 message was consistently detected throughout the small cotyledons (3.0–6.0 mm). These results are consistent with the RNA blot analysis (Example 2).

TABLE 2

Distribution of ADR 12-2 and β-Conglycinin RNA Transcripts in Soybean Seed Determined by Tissue Print Analysis

|  | 3.0–6.0 mm seed | 9.0–11.0 mm seed |
| --- | --- | --- |
| ADR12-2 sense | − | − |
| ADR12-2 antisense | + | + |
| β-conglycinin sense | − | − |
| β-conglycinin antisense | +/− | + |

−: no signal detected
+/−: faint signal detected
+: strong signal detected

EXAMPLE 4

Isolation of the ADR12-2 5'Regulatory Sequence, Intron, and 3' Non-coding Region The seed-enhanced 5' regulatory sequence, intron, and 3' non-coding region of the ADR12-2 gene were isolated and characterized from a Glycine max var. Resnik genomic DNA library purchased from Clontech (catalogue # FL1062j).

5' Regulatory Sequence

The genomic library was plated and screened according to the manufacturer's instructions. The plated library was probed using the ADR12-2 cDNA clone described in Example 2, also according to the manufacturer's instructions. A genomic clone which hybridized to the ADR12-2 cDNA probe was identified, and a λ genomic DNA preparation was made to obtain more DNA, also according to the manufacturer's instructions. Southern analysis (Maniatis et al. (1982), supra) was performed utilizing the ADR12-2 cDNA probe described above, and an ~6 kb PstI/SalI genomic fragment was identified and subcloned into the Stratagene plasmid pBSKS+ for further characterization.

The 5' untranslated region of this fragment was further characterized by restriction enzyme mapping and partial sequence analysis (United States Biolabs Sequenase™ Version 2.0, and Applied Biosystems Prism™ Ready Reaction), according to the manufacturer's instructions. FIG. 4 is a schematic diagram showing various features present in the 5' regulatory sequence. A PstI/SalI genomic fragment which was found to contain an ~5 kb promoter fragment (including 5' untranslated leader region and intron) was subcloned into the PstI and SalI sites of the Stratagene plasmid pBSKS+ for mutagenesis.

Site-directed mutagenesis of the ADR12-2 5' promoter fragment was performed using the mutagenic oligonucleotide of SEQ ID NO:6 and Biorad's Mutagene® system following the manufacturer's instructions, generating an NcoI site at the translational start and a BglII site upstream of the NcoI site (described in detail below in the section entitled "Promoter Fusions").

Further restriction enzyme mapping analysis of the mutagenized promoter fragment identified a HindIII site ~2 kb upstream of the translational initiation site. The approximately 2 kb HindIII/NcoI 5' regulatory sequence (comprising a promoter region, untranslated leader region, and intron) was interrupted by an internal HindIII site. A PstI site was obtained at the 5' end of this 5' regulatory sequence (just upstream of the 5' most HindIII site) through several subclonings. Sequence analysis was performed on this sequence (containing 5' untranslated leader and intron) (United States Biolabs Sequenase™ Version 2.0) according to the manufacturer's instructions. The length of this 5' regulatory sequence was determined to be 2.0 kb. The sequence of this fragment is shown in SEQ ID NO:7. This 2.0 kb 5' regulatory sequence has a PstI site at the 5' end and extends to the putative translation initiation point (modified by placing BglII and NcoI recognition sites at this latter point).

Intron

Comparison of SEQ ID NO:7 to the ADR12-2 cDNA sequence published by Datta et al.( (1993) Plant Molecular Biology 21: 859–869) revealed the presence of an intron in the 5' untranslated leader. An ~0.4 kb insertion within the leader sequence was identified and the sequences around the insertion contain intron splice site consensus sequences. The nucleotide sequence of the intron contained in the 5' untranslated leader of ADR12-2 is shown in SEQ ID NO:8.

3' Non-coding Region

The 3' non-coding region of ADR12-2 was obtained from the genomic clone described above via PCR. The 3' non-coding region of ADR12-2 was obtained from the ~6 kb subcloned λ genomic subcloned PstI and SalI fragment by amplification via PCR using a primer having the sequence shown in SEQ ID NO:9, which amplifies the sense strand of ADR12-2 and places an EcoRI site before the termination codon of ADR12-2 and T3 promoter primer (obtained from New England Biolabs) which is homologous to the region of pBSKS+ directly downstream of the ADR12-2 most 3' end. 100 ng of plasmid DNA containing the ~6 kb ADR12-2 genomic fragment described above was amplified using 50 pmoles of each primer, 0.2 mM dNTPs, and 1× PCR buffer plus $MgCl_2$ (Perkin Elmer) in a total volume of 100 μl. The sample was amplified for 30 cycles (94° C. for 1 minute, 42° C. for 2 minutes, 72° C. for 3 minutes). A 1.2 kb ADR12-2 3' non-coding region fragment which contains an EcoRI site at the 5' end and a SalI site at the 3' end was obtained and verified by sequence analysis (Applied Biosystems Prism™ Ready Reaction) according to the manufacturer's instructions. The nucleotide sequence of this 1.2 kb 3' non-coding region of ADR12-2 is shown in SEQ ID NO:10.

EXAMPLE 5

Transient Expression Analysis of the ADR12-2 Promoter in Soybean

The ADR12-2 5' regulatory sequence was fused to the β-glucuronidase (GUS) gene in plasmid pMON26028 (FIG. 1), and evaluated in a transient assay system in various soybean tissues as well as at various developmental stages of seed. Leaf, stem, small cotyledons (3–5 mm), and large cotyledons (5–8 mm) collected from soybeans (H4994) were bombarded with pMON26028, as well as with pMON8677 (FIG. 2) containing the CaMV 35S promoter, and pMON13773 (FIG. 3) containing the β-conglycinin α' subunit 7s promoter, also fused to Gus.

Tissue Preparation

Tissue was prepared for bombardment by first sterilizing as follows. Seed pods, stem sections, and leaves were soaked in 70% ethanol for 2 minutes, then in 20% bleach for 10 minutes, and finally rinsed four times in sterile distilled water. Leaves and stem sections were then placed on petri dishes containing sterile filters soaked in coculture medium (0.5 mg/ml 6-benzyl amino purine, 3.9 g/l 2-N-morpholino ethane sulfonic acid, and 1/10 concentration of B5 medium (Gamborg et al. (1968) Experimental Cell Research 50: 151–158)). Pods were aseptically opened, the seeds were removed, sized as either small (3–5 mm) or large (5–8 mm), sliced in half, and placed on petri dishes containing sterile filters soaked in coculture medium with the cut edge side up.

Preparation of Plasmid DNAs and Tungsten Particles

Plasmids containing promoters to be evaluated were identical except for the promoter which they included. Each contained the GUS gene and the 3' polyadenylation signal from the nopaline synthase gene. The promoters evaluated were from the ADR12-2 5' regulatory region (also containing 5' untranslated leader region and native intron therein; pMON26028, FIG. 1); Cauliflower Mosaic Virus (CaMV; pMON8677, FIG. 2); and β-conglycinin (pMON13773, FIG. 3).

pMON8677 (FIG. 2) was constructed using well characterized genetic elements. The 0.65 kb enhanced cauliflower mosaic virus 35S RNA promoter containing a duplication of the −90 to −300 region from CaMV (Kay et al. (1987) Science 236: 1299–1302), the 1.9 kb coding sequences from the E. coli β-glucuronidase (GUS) gene (Jefferson et al. (1986) Proceedings of the National Academy of Sciences, USA 83: 8447–8451), and a 0.25 kb fragment containing the 3' polyadenylation sequences from the nopaline synthase (nos) gene (Fraley et al. (1983) Proceedings of the National Academy of Sciences, USA 80: 4803–4807) were each inserted into pUC119 (Yanisch-Perron et al. (1985) Gene 33: 103–119) to produce plasmid pMON8677.

pMON26028 (FIG. 1) was constructed by replacing the e35S promoter of pMON8677 with the ADR12-2 5' regulatory sequences (SEQ ID NO: 7).

pMON13773 (FIG. 3) was constructed by replacing the e35S promoter of pMON8677 with the β-conglycinin α' subunit 7S promoter (Tierney et al. (1987) Planta 172:356–363).

Plasmid DNAs were prepared by standard alkaline lysis followed by CsCl gradient purification (Maniatis et al. (1982), supra). Plasmid DNA was precipitated onto tungsten M10 particles by mixing 25 μl of particles (25 mg/ml in 50% glycerol), 5 μl of plasmid DNA (1 μg/μl), 25 μl 1M CaCl$_2$, and 10 μl 0.1 M spermidine, and vortexing briefly. The particles were allowed to settle for 20 minutes, after which 25 μl of supernatant were removed and discarded. Two independent particle preparations were prepared for each plate of tissue bombarded.

Tissue Bombardment

The particle preparations were then bombarded into the tissue as follows. Each sample of DNA-tungsten was briefly sonicated, and 2.5 μl were bombarded into the tissue contained on one plate using a PDS-1000 Biolistics Particle Gun (DuPont). Two plates of each tissue were each bombarded twice.

Histochemical Staining

Transient GUS gene expression driven by each promoter was determined by histochemical staining (Jefferson et al. (1987) EMBO Journal 6: 3901–3907).

Results

As shown in Table 3, transient expression of the heterologous GUS gene driven by each promoter is consistent with previous RNA blot analysis (Example 2). The ADR12-2 promoter was active in both small (3–5 mm) and large (5–8 mm) soybean seed, and in stem.

TABLE 3

Transient Expression of GUS Driven by Various Promoters in Different Tissues of Soybean

| Promoter | 3–5 mm | 5–8 mm | stem | leaf |
| --- | --- | --- | --- | --- |
| ADR12-2 | + | + | + | +/−* |
| CaMV | + | + | + | + |
| β-Conglycinin | +/− | + | − | − |

*: denotes minimal staining limited to vasculature
−: no detectable staining
+/−: faint staining
+: strong staining

EXAMPLE 6

Transgenic Expression Analysis of the ADR12-2 Promoter and 3' Non-coding Region in Tobacco A double-stranded DNA molecule containing the ADR12-2 promoter fused to GUS with the 3' polyadenylation signal from the nopaline synthase gene (pMON26037 (FIG. 8)) and a double-stranded DNA molecule containing the ADR12-2 promoter fused to GUS with the ADR12-2 3' non-coding region (pMON26035 (FIG. 7)) were used to generate transgenic tobacco plants. The spacial and temporal expression patterns of the reporter gene, β-glucuronidase, was evaluated by histochemical staining.

Preparation of Plasmid DNAs and Agrobacterium tumefaciens containing T-DNA

Plasmids containing either the ADR12-2 5' regulatory sequences (pMON26037 (FIG. 8)) or containing the ADR12-2 5' regulatory sequences and ADR12-2 3' non-coding region (pMON26035 (FIG. 7)) were identical with the exception of the 3' non-coding regions.

pMON26037 (FIG. 8) was constructed by subcloning the 4.2 kb NotI fragment from pMON26028 (FIG. 1) containing the ADR12-2 5' regulatory sequences fused to GUS with the NOS polyadenylation signal into the plant transformation vector pMON17227 (WO92/04449) (FIG. 6) which contains a gene encoding an enzyme conferring glyphosate resistance for selection in plants.

pMON26035 (FIG. 7) was constructed by first replacing the NOS 3' polyadenylation signal in pMON26028 (FIG. 1) with the ADR12-2 3' non-coding region (SEQ ID NO:10) to create pMON26032 (FIG. 5). pMON26035 (FIG. 7) was constructed by subcloning the 5.1 kb NotI fragment containing the ADR12-2 5' regulatory sequences fused to GUS with the ADR12-2 3' non-coding region from pMON26032 into the plant transformation vector pMON17227.

pMONs 26035 (FIG. 7) and 26037 (FIG. 8) were then mated into Agrobacterium tumefaciens.

Transformation and Regeneration of Transgenic Tobacco

Tobacco (Samsun) was transformed with Agrobacterium tumefaciens containing either pMON26035 (FIG. 7) or pMON26037 (FIG. 8).

Stock material for explants was prepared by first surface sterilizing seed by soaking them in a 20% chlorox solution, containing Tween 20 surfactant, for 30 minutes. The seeds were then rinsed three times with sterile deionized water Approximately 50 seed were plated per phytatray containing MSO (4.4 g/l MS basal salts +B5 vitamins (Sigma), and 30 g/l sucrose; at pH5.7), with 0.9% agar. Pytatrays containing seed were cultured at 25° C., 24 hours continuous cool white light, 40–50 microeinsteins. After 3–4 weeks, tissue was harvested by cutting seedlings off at the base and placing them in a petri plate with 1–2 mls TXD liquid media (4.3 g/l Gibco MS, 2ml/l of 1× B5 medium (Gamborg et al. (1968), supra), 8 ml/l of 0.5 mg/ml parachlorphenoxy acetic acid, 0.01 ml/l of 0.5 mg/ml kinetin, and 30 g/l sucrose; at pH 5.7) to inhibit drying. This tissue was then diced into pieces, and placed on solid pre-culture plates (MS 104 media (4.4 g/l MS basal salts +B5 vitamins (Sigma), 30 g/l sucrose, 1.0 mg/l benzyladenine, 0.1 mg/l napthalene acetic acid, and 9 g/l agar; at pH 5.7) containing a sterile Whatman filter with 2 ml of TXD liquid media (described above). These explants were precultured under the same conditions described above.

After pre-culture, any explants containing visible shoot tips were discarded. The remaining tissue was inoculated by pipetting liquid suspension of Agrobacterium containing plasmids directly onto the pre-culture plates covering the explant tissue. The Agrobacterium was left on the plates for 15 minutes an d was then removed. These explants were then co-cultured on these same plates for 2–3 days.

The explants were then transferred to MS104 (described above) also containing 500 mg/l carbenicillin, 100 mg/l cefotaxime, 150 mg/l vancomycin, for a delay phase of three days. The explants were then transferred to glyphosate selection medium (MS104 (described above) containing 0.05 mM glyphosate, 500 mg/l carbenicillin, 100 mg/l cefotaxime, and 150 mg/l vancomycin) for selection and regeneration of transgenic cells. Once shoots elongated and had an apical meristem, they were excised from the callus and cultured on MSO (described above) containing 500 mg/l carbenicillin and allowed to root before transfer to soil.

Histochemical Staining

Transgenic GUS protein expression produced from the ADR12-2 5' regulatory sequences, GUS coding sequence and NOS 3' polyadenylation sequence or ADR12-2 3' non-coding region were determined by histochemical staining (Jefferson et al. (1987), supra). The tissue to be evaluated was removed from the transgenic $r_0$ tobacco plants and scored histochemically. Six lines containing T-DNA from pMON26037 (FIG. 8) and 17 lines containing T-DNA from pMON26035 (FIG. 7) were expressing GUS by histochemical staining. The data from these lines is described below.

Results

As shown in Table 4, transgenic expression of GUS driven by the ADR12-2 5' regulatory sequences with either the NOS polyadenylation signal or the 3' non-coding sequences of ADR12-2 is consistent with previous RNA blot analysis (Example 2) and with transient expression analysis (Example 5). The ADR12-2 regulatory sequences are expected to express genes in a seed enhanced manner. Expression in seed is expected to begin early in development. No leaf expression is expected. As shown in Table 4 the majority of the lines expressed at the earliest seed developmental time point evaluated (~92%); whereas, relatively few lines expressed in leaf (~12.5%).

TABLE 4

Transgenic Expression of GUS Driven by the ADR12-2 Promoter in Various Tobacco Tissues

| Plasmid | seed (12 dpa) | leaf |
|---|---|---|
| 26035 | 100% | 25% |
| 26037 | 83% | 0% | percentages indicated above represent the percent of lines expressing GUS in the tissue indicated.

EXAMPLE 7

Isolation of Homologous Promoter Regions From Other Plants

Promoter regions biologically capable equivalent to that disclosed herein, i.e., capable of driving gene expression during early seed development, can be identified in and isolated from plants other than soybean by a variety of different methods. Three such methods are described below.

Hybridization

Plant genomic DNA can be analyzed for related 5' regulatory sequences by Southern blotting and probing with radiolabeled probe prepared from ADR12-2 cDNA (Maniatas et al. (1982), supra). Hybridization of the probe can be performed overnight at 45° C. in 6× SSC, 0.01M EDTA, 5× Denhardt's solution, 0.5% SDS, and 100 μg/ml salmon sperm DNA. Subsequent washes can be performed at 45° C. in 6× SSC and 0.2% SDS for 15 minutes.

If hybridization of radiolabeled probe prepared from ADR12-2 cDNA to plant genomic DNA proves unsuccessful, a cDNA library can be prepared from plant mRNA. This cDNA library can then be probed under the conditions described above. This cDNA library can then be probed under the conditions described above. Homologous cDNA identified in this way can then be used as a probe in Southern analysis of a genomic DNA library from the plant.

In either of the foregoing cases, the ADR12-2 cDNA probe should hybridize well with clones from closely related species.

Immunological Detection

For species which are evolutionarily divergent from soybean, an alternative method would be to use an antibody raised against the gene product of ADR12-2. This antibody can be used to screen a cDNA expression library in, for example, λ gt11. In this manner, a cDNA clone can be obtained for the new species. This cDNA clone can then be used to isolate the corresponding genomic clone from a genomic library of this species by standard DNA hybridization techniques.

Using either soybean ADR12-2 cDNA or homologous cDNA from another plant as a probe, a genomic clone comprising a 5' regulatory sequence promoter region homologous to that disclosed herein can be identified and the utility thereof analyzed as described in the foregoing Examples.

PCR Amplification

PCR amplification can be used to obtain DNA fragments that are homologous to the ADR12-2 coding sequence (Datta et. al (1993) Plant Molecular Biology 21: 859–869) from a plant species of choice. This PCR fragment can be used to identify a gene (including the promoter associated with the coding sequence) that is expressed in seed. The template for PCR can be derived from a variety of sources, including genomic DNA, DNA isolated from genomic libraries, DNA isolated from cDNA libraries, phage DNA from bacteriophage genomic and cDNA libraries (Maniatis, supra), and RNA (Kawasaki (1990) PCR Protocols: A Guide to Methods and Applications, pp. 21–27; Frohman (1990) Id., pp. 28–38).

To identify and isolate PCR fragments homologous to the soybean ADR12-2 sequences from the chosen plant species, two oligonucleotide primers similar to soybean ADR12-2 sequences, or at least one oligonucleotide primer prepared from the nucleotide sequence of degenerate oligonucleotide sequences inferred from the predicted amino acid sequence, can be used. An example of the conditions useful for isolation of sequences similar to ADR12-2 sequences using template obtained from any of the sources above with primer sequences similar to ADR12-2 coding sequence is described in Example 2 ("Probe Preparation and Hybridization").

EXAMPLE 8

Use of the ADR12-2 5' Promoter Region For Expression of Heterologous Genes in Plants The present early seed promoter region can be used to drive the expression of target genes in seeds of a variety of monocotyledonous and dicotyledonous plants, including, for example, soybean, other legumous plants, canola, cotton, flax, sunflower, and tobacco. Promoter elements that regulate gene expression often share homology. For example, an RY element within the legumin box (Lelievre et al. (1992) Plant Physiology 98: 387–391) has been determined to play an important role in regulating the level of seed expression. This RY element has also been identified in the soybean glycinin promoter (Asako et al. (1995) Plant Cell Reports 14: 539–544) and the soybean β-conglycinin promoter (Lessard et al. (1993) Plant Molecular Biology 22: 873–885).

In addition, promoters from one plant species often function in other plant species. For example, the EMU promoter from wheat, the polyubiquitin promoter from maize, and the actin promoter from rice all drive transient gene expression in maize and barley cell cultures (Schledzewski et al (1994) Transgenic Research 3: 249–255). In another example, the glutelin promoter from rice (Leisy et al. (1989) Plant Molecular Biology 14: 41–50) and the acyl carrier protein promoter from Arabidopsis (Baerson et al. (1993) Plant Molecular Biology 22: 255–267) both drive expression in transgenic tobacco plants.

In view of the foregoing, one would fully expect the ADR12-2 promoter region and related regulatory sequences to function in a wide variety of plants other than soybean.

Another class of target genes whose expression can be driven by the present promoter includes genes that encode enzymes involved in, or which can be used in, the biosynthesis of polyhydroxyalkanoates (PHAs), which are a family of useful, biologically produced, biodegradable polyesters. A number of PHA biosynthetic genes have been identified, including:

1) β-ketothiolases;
2) 3-hydroxya-acyl-CoA reductases;
3) PHA synthases;
4) threonine deaminases, which produce α-ketobutyrate from threonine;
5) trans-2,3-enoyl-CoA hydrases, which produce D-3-hydroxy-acyl-CoA from trans-2,3-enoyl-CoA;
6) trans-2,3-enoyl-CoA reductases, which reduce trans-2,3-enoyl-CoA, producing acyl-CoA; and
7) ACP/CoA acyltransferases, which convert metabolites formed during fatty acid biosynthesis to acyl-CoA for utilization as substrates in polymer production.

Promoter Fusions

The expression of coding sequences of interest can be placed under the control of the ADR12-2 5' regulatory region by fusing these coding sequences thereto. Site-directed mutagenesis of the ADR12-2 5' promoter fragment was performed using the mutagenic oligonucleotide of SEQ ID NO:6 and BIORAD's Mutagene® system following the manufacturer's instructions, generating an NcoI site at the translational start (denoted by the asterisk) and a BglII site upstream of the NcoI site. By adding a BglII site upstream from the translational start site of a coding sequence of interest, or by mutagenizing the sequence in the vicinity of the translational start site of a coding sequence of interest to create an NcoI site while maintaining the proper reading frame, any coding sequence can be placed under the control of the ADR12-2 promoter.

```
ADR12-2:               5' a t t t g c a a g atg* g 3'        (SEQ ID NO:11)

Mutagenized Sequence:  5' a g a t c t a c c atg*g 3'         (SEQ ID NO:12)

BglII site:            5' a g a t c t 3'

NcoI site:             5' c c atg*g 3'

Plants
```

Target Genes

The ADR12-2 promoter region disclosed herein can be used to drive the expression of any gene(s) the product(s) of which is(are) desirably synthesized and/or accumulated in plant seeds.

One class of target genes the expression of which can be driven by the present promoter region includes genes that either increase oil content or improve oil quality in seed. For example, fatty acid desaturases expressed in antisense would decrease the number of double bonds in the fatty acid side chains, thereby improving oil quality. A number of desaturases useful for antisense expression in this manner have been identified. These include:

1) stearoyl ACP desaturase, which converts stearic acid to oleic acid;
2) oleoyl PC desaturase, which converts oleic acid to linoleic acid; and
3) linoleoyl PC desaturase, which converts linoleic acid to linolenic acid.

Plants in which the present promoter can be used to drive expression in seeds of DNAs encoding enzymes such as those listed above include both monocots and dicots. Non-limiting examples of such plants include Arabidopsis, cotton, potato, tobacco, wheat, and high oil seed plants such as corn, soybean, other leguminous plants, canola, oil seed rape, sunflower, flax, and peanut.

The invention being thus described, it will be obvious that the same can be varied in many ways. Such variations are not to be regarded as a departure from the spirit and scope of the invention, and all such modifications as would be obvious to one skilled in the art are intended to be included within the scope of the following claims.

What is claimed is:

1. An isolated DNA molecule comprising SEQ ID NO:7.

2. An isolated nucleic acid molecule comprising the nucleotide sequence shown in SEQ ID NO:10.

3. A recombinant, double-stranded DNA molecule expressible in plant cells, comprising operatively linked in sequence in the 5' to 3' direction:

(a) an auxin down-regulated 5' regulatory sequence that directs transcription of a gene throughout seed development in plants, wherein said 5' regulatory sequence comprises SEQ ID NO:7;

(b) a structural DNA sequence that encodes an RNA sequence which encodes a desired protein, or a structural DNA sequence that encodes an RNA sequence in the antisense orientation; and (c) a 3' non-coding region which encodes a polyadenylation signal which functions in plant cells to cause transcriptional termination and the addition of polyadenylate nucleotides to the 3' end of said RNA sequence which encodes a desired protein or to the 3' end of said RNA sequence in the antisense orientation;

wherein said 5' regulatory sequence is heterologous with respect to said structural DNA sequence.

4. The DNA molecule of claim 3, further comprising a 3' non-coding region involved in effecting higher levels of transcriptional activity of said 5' regulatory sequence.

5. A transformed plant cell, comprising a recombinant, double-stranded DNA molecule expressible in plant cells, comprising operatively linked in sequence in the 5' to 3' direction:

(a) an auxin down-regulated 5' regulatory sequence that directs the transcription of a gene throughout seed development in plants, wherein said 5' regulatory sequence comprises SEQ ID NO:7;

(b) a structural DNA sequence that encodes an RNA sequence which encodes a desired protein, or a structural DNA sequence that encodes an RNA sequence in the antisense orientation; and (c) a 3' non-coding region which encodes a polyadenylation signal which functions in plant cells to cause transcriptional termination and the addition of polyadenylate nucleotides to the 3' end of said RNA sequence which encodes a desired protein or to the 3' end of said RNA sequence in the antisense orientation;

wherein said auxin down-regulated 5' regulatory sequence is heterologous with respect to said structural DNA sequence.

6. The plant cell of claim 5, further comprising a 3' non-coding region involved in effecting higher levels of transcriptional activity of said 5' regulatory sequence.

7. A transgenic plant, the cells of which comprise a recombinant, double-stranded DNA molecule expressible in plant cells, comprising operatively linked in sequence in the 5' to 3' direction:

(a) an auxin down-regulated 5' regulatory sequence that directs the transcription of a gene throughout seed development in plants, wherein said 5' regulatory sequence comprises SEQ ID NO:7;

(b) a structural DNA sequence that encodes an RNA sequence which encodes a desired protein, or a structural DNA sequence that encodes an RNA sequence in the antisense orientation; and (c) a 3' non-coding region which encodes a polyadenylation signal which functions in plant cells to cause transcriptional termination and the addition of polyadenylate nucleotides to the 3' end of said RNA sequence which encodes a desired protein or said RNA sequence in the antisense orientation;

wherein said 5' regulatory sequence is heterologous with respect to said structural DNA sequence.

8. The plant of claim 7, further comprising a 3' non-coding region involved in effecting higher levels of transcriptional activity of said 5' regulatory sequence.

9. The plant of claim 7, wherein the plant is soybean, legume, canola, cotton, flax, sunflower, tobacco, Arabidopsis, potato, wheat, corn, or peanut.

10. A method of expressing a gene in a transgenic plant, comprising:

(a) transforming plant cells with a DNA molecule comprising operatively linked in sequence in the 5' to 3' direction:

(i) an auxin down-regulated 5' regulatory sequence that directs the transcription of a gene throughout seed development in plants, wherein said 5' regulatory sequence comprises SEQ ID NO:7;

(ii) a structural DNA sequence that encodes an RNA sequence which encodes a desired protein, or a structural DNA sequence that encodes an RNA sequence in the antisense orientation; and (iii) a 3' non-coding region which encodes a polyadenylation signal which functions in plant cells to cause transcriptional termination and the addition of polyadenylate nucleotides to the 3' end of said RNA sequence which encodes a desired protein or said RNA sequence in the antisense orientation;

wherein said auxin down-regulated 5' regulatory sequence is heterologous with respect to said structural DNA sequence;

(b) regenerating plant cells that have been transformed to produce differentiated plants; and (c) selecting a transformed plant which expresses said structural DNA sequence.

11. A method of expressing a gene in a transgenic plant comprising the steps of:

(a) transforming plant cells with a DNA molecule comprising operatively linked in sequence in the 5' to 3' direction:

(i) an auxin down-regulated regulatory sequence that directs transcription of a gene throughout seed development in plants, wherein said regulatory sequence comprises SEQ ID NO:7;

(ii) a structural DNA sequence that encodes an RNA sequence which encodes a desired protein; and (iii) a 3' non-coding region which encodes a polyadenylation signal which functions in plant cells to cause transcriptional termination and the addition of polyadenylate nucleotides to the 3' end of said RNA sequence which encodes a desired protein;

(b) regenerating plant cells that have been transformed to produce differentiated plants; and (c) selecting a transformed plant which expresses said structural DNA sequence.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:1:

GGAGCGGCCG CTCGAGAATT CTTTTTTTTT TTTTT                        35

(2) INFORMATION FOR SEQ ID NO:2:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:2:

GGAGCGGCCG CTCGAGAATT CCCCCCCCCC CCCCC                        35

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:3:

GGAGCGGCCG CTCGAGAATT CC                                     22

(2) INFORMATION FOR SEQ ID NO:4:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:4:

GATGTCGACA TGATGAGAGC GCGGTTCCCA T                              31

(2) INFORMATION FOR SEQ ID NO:5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:5:

GATGAATTCT TCACTTCCCT TTCCTCCGT                                               29

(2) INFORMATION FOR SEQ ID NO:6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:6:

CCATGGTAGA TCTTAACTTC GAATTCGGAA G                                            31

(2) INFORMATION FOR SEQ ID NO:7:

(i) SEQUENCE CHARACTERISTICS:
        (A) LENGTH: 2030 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:7:

CTGCAGGAAT TCGATATCAA GCTTGCTACT TGGCTTTCAC GTAACATACC AGGTTCAGTA      60

TCCAACTAAC ATATCAATTC ATTATTGTTG TTGTGATTCA AATTCATAAA TAAACCTCCT     120

TTCATTTAAT ATTCTAAATT TCACTTACCA TGAAGATTTC ATCTCACTGG AAACCCCCAC     180

TCAATTAATA TCTAAATTTT CACTTGCCTA TATTTTGAA AGGTAATTTT CACTTACCTT      240

AAACACCTCA TCCTTTGTTT CTCTTTGCAT TCAATTAACC CCACTTTGTG CCACTCTGGT     300

TTTTAATTCT CGATAATTTT GTATCGATCA AATTTGCATG CATAGTATTT CATTCTTCTC     360

TCATATTTCT TTTGGGCAGG TTTTCCCAAT TCAACGTAAA GGTGCAATGG GTATCGAGAA     420

GGCTCAAATC AACATTGTGG TGGTTGGTTA TGTGGACTCT AAGAAGTTAA GGAACTCAAT     480

AAGCCTGTTG CTGAGAGACA AATTGCTGTC ATTAACTTAA CTGCCAAATA TAAGGCATGA     540

CCATCACACC AACCTTAAAA ACTAGTTTAT CACAATTAAC TTAATTACTT TCATTAATT      600

TAATTTCAAT TAAAAGGGA AAAATTTATT TTACTTGTTA TTTATATTAC ATTTATTTTA      660

AAAATTAAAA AATTATCATT ATAATATATT TATTTTCCTT TCTATTTCAT TTTTATTAAT     720

TTTTTAGTTT TATTTTCATT CTTATTCTAT TATTATTTAT TATTTTTCAT TTATCTCTGT     780

TTTAATTTAT TATTATTTTT ACTATTATCT CTATTTTATT ATCGCTGATA CACGATACAC     840

CCAAGAATAG GATATGACTA CCATAGTAAT TTTCCTTTTA TGAAGATGCA GGTACCCTGT     900

ACACCCAACA AAAATAAATT AGTATGCATT ATTGTACCTT TAATCATATC AAAGATCTAC     960

ACAAAATAAA TTAATCCACC TTGTCGGTTG ATGATAACAT CAGTGTGCAT TATCGCACTA    1020

TGTCAGTCGG GGTAGGTGTA ATAGGTTCTT CTAAAATTTG AAAGGGTTGA TTATGTTTTT    1080

GTTATTTTTT TATTAAATAA TTAAATTAGT CCTTAAGATT GTCATATTAA TTAATTTTTA    1140

TCCAAAAATT ATGAGAAACT CAAATGAGTC TCATATTTTT TTTAAGATAT TAGCTACATC    1200

TCGATTATAA AAAAACATT ATTTATATTT ATTAAAGAAA TTAGTTAATT TTATTAAATT     1260

GAGTTATTTT TAATTTTTTA ATTAATTTTT ATTTAAACTT GATATTAAAT ATAAAAAAAT    1320

```
TGATCTTATT AAATGAAAAT TATTTTTAAA ATAATCTTAT TAAATAAGAT TTTAATAATT      1380

GAAATTTATT TATTTGTTTA TATTTGAGAT TTGGAAGGTG TAAGTCTCCA AAAAGTTCTT      1440

ATTTTTTGTT TTGGATTCAT GTGATATTAT TATACTTAAA TTCGTATAAA TTACGAAGTA      1500

AAAATGAAGG TTATATTCAT AAATACAAAC TATGAGTTGG TCTATAAATA ACGTTCAAGT      1560

CCCTCTTCTT CGTCACAGCT ATTCCTCTTA AGCTTGCTAC TGAGTTTCCA CATTGCATAC      1620

CTTAGGTTCA TTCTCTGACT AGCTTTTAAT TTTTCTCTTT ACGAGTTTAT TAATTATTGT      1680

TGTTGTGATT CAAATATCAT AAACCTCCAC TCAATTAATA TTTTAATTTT CACTTACCCT      1740

AAACACTTCA TCTCACTGTA AACCTTATAT AATTTACTCA ATTAATATTC AAGTTAATTT      1800

TCAGTTTTAA CTTACCTTAT ACAAGCACTT GATCTCATTG TTTAGATTCT CTTTGCATCT      1860

AACTAACCCT ATTTTGTGCC ACTCTAGCTT GTTTCTAATA TTCTTGGAGG TGTTGTATTG      1920

TACAAATTAA TTTTGCATGC AGTATATGTA TATATATTTC ATATTTTTTT CTGATTATAT      1980

TAATTTATTT TGGACAGGTC TTCCGAATTC GAAGTTAAGA TCTACCATGG                 2030

(2) INFORMATION FOR SEQ ID NO:8:

(i) SEQUENCE CHARACTERISTICS:
        (A) LENGTH: 372 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:8:

GTTCATTCTC TGACTAGCTT TTAATTTTTC TCTTTACGAG TTTATTAATT ATTGTTGTTG        60

TGATTCAAAT ATCATAAACC TCCACTCAAT TAATATTTTA ATTTTCACTT ACCCTAAACA       120

CTTCATCTCA CTGTAAACCT TATATAATTT ACTCAATTAA TATTCAAGTT AATTTTCAGT       180

TTTAACTTAC CTTATACAAG CACTTGATCT CATTGTTTAG ATTCTCTTTG CATCTAACTA       240

ACCCTATTTT GTGCCACTCT AGCTTGTTTC TAATATTCTT GGAGGTGTTG TATTGTACAA       300

ATTAATTTTG CATGCAGTAT ATGTATATAT ATTTCATATT TTTTCTGAT TATATTAATT        360

TATTTTGGAC AG                                                          372

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:9:

CTCCAGGGCA TGAATTCTGA GGGCATG                                           27

(2) INFORMATION FOR SEQ ID NO:10:

(i) SEQUENCE CHARACTERISTICS:
        (A) LENGTH: 1183 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:10:
```

```
GAATTCTGAG GGCATGCACG CACGGNCTCG GAGGGGAACC AGAAAATTAT GTTAACAAAA      60

TAATCTGGAA CCCTAATGTA TCAGNGTCAT CATCAGTGTG TAGTTTAAGC TAGCTTTGNT     120

ATGGTTACGT TCTCTGAGAT GAGAGTCTTG CATGAACAGT GCCATTCTGA TGTATTGCTT     180

TCCTTGAAAG TTAATGCATG CTTCTTATCT TCTGTCTAAA GCTATATGCT TTCTTTNNCT     240

TTTNCTTTTT GGNNAATCAG AACATTTGCA ACTTCACTCC TTAGTATATA ATAGTTATCC     300

ATACAAAAG  AAATATTATT TAAGGACATA CTGAAACATA AATATTACAC TNTTTAGCAT     360

CCATAAAAAA AAATTGAACG AGGAGGGTTA AAAATATATT TTTAACATNT NNTTAATATA     420

TTCTTTGNTA TTGATTGAAT TTAAAAAAAA ATATAAAATT AGCTAGAGAG AAAATTATNA     480

AATAAAATAT AACCTTAAAA ATTTATAATA TTTAATAAAT NTTAATCAAT TAAAAAGAAC     540

ACTCCTCCAG ACTTAAGATT TGGGGTTGGA TTAATTCACT AGTAAGTACA TCATTAAGAT     600

TCATTCGATT CANTGCAGCG GACANGGGAA ATAAAAGAAA ATACTATATG TGGGTTTNTT     660

TACTACAAGA AATATTATCT ATGTCTACGG ACAAAAACCA TCACTAGATG TTAAAAATGT     720

GTAGGTAAAT ATAATAAAAA TTTGGTCCTA CAGACATTGT GGTCGTCAAC TTTGAGGGGA     780

CGCATGTGAC ACCCTCTATC CCTCACATAT ATACTAACAA AGGAATAAAA ATTCAAATAT     840

TAATTAAAAG TATTTTTTTN GNNCATTTTT AAATACGGGT CTTTCAAAGG GATAAAAGG      900

TCACAATCAC TTTCTTCTAC ATCATATTCA AACTTGTCCA AATAAATAAT AAAGTCATCG     960

GCTCGAACAA GGTCGTTTGA GACTTCATAC AATTAATATA AAACCTATAC CCCAATGTCA    1020

CATCCTATCA GAGCGTTGTG TCTCGACGTC TTTCAGCACA ATATTCCTTA AAGCAGGTTA    1080

CCTAGTCATC TTGCTCCCCC GACACAGAGT CCAAGATCAT CACAGGGATC CTCCGAGCTC    1140

TTCTNTAGTG TCANCTAAAT GGCCATTTAG GCCTAGAGTC GAC                     1183
```

(2) INFORMATION FOR SEQ ID NO:11:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

ATTTGCAAGA TGG                                                         13

(2) INFORMATION FOR SEQ ID NO:12:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

AGATCTACCA TGG                                                         13